United States Patent
Wang et al.

(10) Patent No.: US 9,545,199 B2
(45) Date of Patent: Jan. 17, 2017

(54) APPARATUS AND METHODS FOR DETECTING OPTICAL COMPONENTS AND THEIR MISALIGNMENT IN OPTICAL COHERENCE TOMOGRAPHIC SYSTEMS

(71) Applicant: Carl Zeiss Meditec, Inc., Dublin, CA (US)

(72) Inventors: Yingjian Wang, Fremont, CA (US); Homayoun Bagherinia, Oakland, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 56 days.

(21) Appl. No.: 14/489,352

(22) Filed: Sep. 17, 2014

(65) Prior Publication Data
US 2015/0085294 A1    Mar. 26, 2015

Related U.S. Application Data

(60) Provisional application No. 61/881,790, filed on Sep. 24, 2013.

(51) Int. Cl.
*G01B 9/02*     (2006.01)
*A61B 3/10*     (2006.01)

(52) U.S. Cl.
CPC .......... *A61B 3/102* (2013.01); *G01B 9/02068* (2013.01); *G01B 9/02072* (2013.04); *G01B 9/02091* (2013.01)

(58) Field of Classification Search
CPC ..... G01M 11/00; G01M 11/0271; A61B 3/12; G01B 9/02062; G01B 9/02063; G01B 9/02091

USPC .................................................. 356/479, 497
See application file for complete search history.

(56) References Cited

U.S. PATENT DOCUMENTS

| | | |
|---|---|---|
| 5,321,501 A | 6/1994 | Swanson et al. |
| 6,095,648 A | 8/2000 | Birngruber et al. |
| 7,830,525 B2 | 11/2010 | Buckland et al. |
| 2005/0105047 A1 | 5/2005 | Smitth et al. |
| 2007/0291277 A1 | 12/2007 | Everett et al. |
| 2008/0106696 A1 | 5/2008 | Buckland et al. |
| 2010/0181462 A1* | 7/2010 | Sugita ............... G01B 9/02044 250/201.8 |
| 2010/0226554 A1* | 9/2010 | Suehira .................. A61B 3/102 382/131 |
| 2011/0051086 A1 | 3/2011 | Takai et al. |

(Continued)

FOREIGN PATENT DOCUMENTS

| | | |
|---|---|---|
| EP | 2130486 A1 | 12/2009 |
| WO | 2010/006785 A1 | 1/2010 |

(Continued)

OTHER PUBLICATIONS

International Search Report & Written Opinion received for PCT Patent Application No. PCT/EP2014/070209, mailed on Feb. 12, 2015, 14 pages.

(Continued)

*Primary Examiner* — Jonathan Hansen
(74) *Attorney, Agent, or Firm* — Morrison & Foerster LLP

(57) ABSTRACT

Systems and methods are presented which allow the detection of the presence, type, and misalignment of optical components in the optical train of an optical coherence tomographic instrument to be determined from the use of OCT depth information.

17 Claims, 8 Drawing Sheets

(56) References Cited

U.S. PATENT DOCUMENTS

| | | |
|---|---|---|
| 2011/0102802 A1 | 5/2011 | Izatt et al. |
| 2011/0176111 A1 | 7/2011 | Taki et al. |
| 2011/0267583 A1 | 11/2011 | Hayashi |
| 2011/0299034 A1 | 12/2011 | Walsh et al. |
| 2012/0262720 A1 | 10/2012 | Brown et al. |
| 2012/0274898 A1* | 11/2012 | Sadda .................. A61B 3/102 351/206 |
| 2013/0162978 A1 | 6/2013 | Yazdanfar et al. |
| 2013/0208240 A1 | 8/2013 | Sharma et al. |
| 2013/0235343 A1 | 9/2013 | Hee et al. |
| 2013/0258349 A1 | 10/2013 | Makihira et al. |
| 2013/0286348 A1 | 10/2013 | Makihira et al. |
| 2013/0293838 A1 | 11/2013 | Makihira et al. |
| 2014/0268039 A1 | 9/2014 | Arianta et al. |

FOREIGN PATENT DOCUMENTS

| | | |
|---|---|---|
| WO | 2011/037980 A2 | 3/2011 |
| WO | 2011/037980 A8 | 4/2011 |
| WO | 2011/037980 A3 | 6/2011 |

OTHER PUBLICATIONS

Invitation to pay additional fees received for PCT Patent Application No. PCT/EP2014/070209, mailed on Dec. 8, 2014, 4 pages.
Non-Final Office Action received for U.S. Appl. No. 13/803,522, mailed on Jun. 5, 2014, 11 pages.
Invitation to pay additional fees received for PCT Patent Application No. PCT/EP2014/055079, mailed on Jul. 9, 2014, 6 pages.
Benes et al., "Corneal Shape and Eccentricity in Population", Coll. Antropol., vol. 37, Suppl. 1, 2013, pp. 117-120.
Canny, John, "A Computational Approach to Edge Detection", IEEE Transactions on Pattern Analysis and Machine Intelligence, vol. 8, No. 6, Nov. 1986, pp. 679-698.
Choma et al., "Sensitivity Advantage of Swept Source and Fourier Domain Optical Coherence Tomography", Optics Express, vol. 11, No. 18, Sep. 8, 2003, pp. 2183-2189.
Fischler et al., "Random Sample Consensus: A Paradigm for Model Fitting With Applications to Image Analysis and Automated Cartography", SRI International, Mar. 1980, 41 pages.
Gatinel et al., "Corneal Asphericity Change after Excimer Laser Hyperopic Surgery: Theoretical Effects on Corneal Profiles and Corresponding Zernike Expansions", Investigative Ophthalmology & Visual Science, vol. 45, No. 5, May 2004, pp. 1349-1359.
Gatinel et al., "Corneal Elevation Topography: Best Fit Sphere, Elevation Distance, Asphericity, Toricity, and Clinical Implications", Cornea, vol. 30, No. 5, 2011, pp. 508-515.
Gatinel et al., "Etude Des Parametres Permettant la Description Mathematique De l'asphericite Corneenne", J. Fr. Ophtalmol, vol. 25, No. 1, 2002, pp. 81-90.
Gonzalez-Meijome et al., "Asphericity of the Anterior Human Cornea with Different Corneal Diameters", J. Cataract Refract Surg., vol. 33, 2007, pp. 465-473.
Hee et al., "Optical Coherence Tomography for Ophthalmic Imaging: New Technique Delivers Micron-Scale Resolution", IEEE Engineering in Medicine and Biology, vol. 14, Issue 1, Jan./Feb. 1995, pp. 67-76.
Huang et al., "Optical Coherence Tomography", Science, vol. 254, Nov. 22, 1991, pp. 1178-1181.
Klein, Stanley A., "Axial Curvature and the Skew Ray Error Corneal Topography", Optometry and Vision Science, vol. 74, No. 11, 1997, pp. 931-944.
Klein, Stanley A., "Corneal Topography: A Review, New ANSI Standards and Problems to Solve", OSA Tops, vol. 35, Vision Science and Its Applications, 2000, pp. 286-296.
Klein et al., "Shape and Refractive Powers in Corneal Topography", Investigative Ophthalmology & Visual Science, vol. 36, No. 10, Sep. 1995, pp. 2096-2109.
Lee et al., "In vivo Optical Frequency Domain Imaging of Human Retina and Choroid", Optics Express, vol. 14, No. 10, May 15, 2006, pp. 4403-4411.
Leitgeb et al., "Ultrahigh Resolution Fourier Domain Optical Coherence Tomography", Optics Express, vol. 12, No. 10, May 17, 2004, pp. 2156-2165.
Nassif et al., "In Vivo Human Retinal Imaging by Ultrahigh-Speed Spectral Domain Optical Coherence Tomography", Optics Letters, vol. 29, No. 5, Mar. 1, 2004, pp. 480-482.
Qiu, Jeff, "Cirrus Alignment/Calibration Review", Oct. 4, 2010, 27 pages.
Ralston et al., "Interferometric Synthetic Aperture Microscopy", Nature Physics, vol. 3, Feb. 2007, pp. 129-134.
Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.

\* cited by examiner

501 Anterior Corneal Surface

502 Posterior Corneal Surface

601 Anterior Corneal Surface

602 Posterior Corneal Surface

701 Circumference associated with Zone diameter

701 Circumference associated with Zone diameter

APPARATUS AND METHODS FOR DETECTING OPTICAL COMPONENTS AND THEIR MISALIGNMENT IN OPTICAL COHERENCE TOMOGRAPHIC SYSTEMS

PRIORITY

This application claims priority under 35 USC §119 from provisional application Ser. No. 61/881,790 filed Sep. 24, 2013, the disclosure of which is herein incorporated in its entirety.

TECHNICAL FIELD

This application presents an apparatus and a method for detecting the presence and misalignment of one or more lenses in the optical train of an optical coherence tomographic instrument.

BACKGROUND

Optical Coherence Tomography (OCT) is a technology for performing high-resolution cross sectional imaging that can provide images of tissue structure on the micron scale in situ and in real time. OCT is a method of interferometry that uses light containing a range of optical frequencies to determine the scattering profile of a sample. The axial resolution of OCT is inversely proportional to the span of optical frequencies used. OCT technology has found widespread use in ophthalmology for imaging different areas of the eye and providing information on various disease states and conditions. Commercial OCT devices have been developed for imaging both the anterior and posterior sections of the eye (see for example Cirrus HD-OCT, Visante Omni, and Stratus (Carl Zeiss Meditec, Inc. Dublin, Calif.)). The Cirrus HD-OCT system allows for imaging both the anterior and posterior regions by inserting a lens to change the focal properties of the system as described in US Publication No. 20070291277. In addition to collecting data at different depths or locations, different scan patterns covering different transverse extents can be desired depending on the particular application.

Although imaging the retina in the posterior segment is concerned important for most major diseases of the eye, often it is desired to obtain OCT images on the cornea, which is in the anterior segment. One approach to this is to insert a diverging lens (or lenses) into the OCT optical train so as to form a virtual point source near the pupil conjugate. This results in a beam waist near the pupil of the subject. The power of the lens can be set so that the beam waist is on the cornea of a typical eye. Portions of the optical train are then moved along the optical axis by a typical eye length simultaneously with the addition of the lens, so as to quickly switch between retinal and a variety of corneal OCT imaging modalities. One type of add-on lens could be used for pachymetry measurements and narrows the field-of-view (FOV). Alternatively, sometimes a FOV wider than is available with the primary lens is desired which can be achieved by a different lens.

Precise knowledge of the optical train, including but not limited to the existence, identity, and location of optical components and their alignments, is an important aspect in ophthalmic optical coherence tomographic systems, where light is directed to an eye of a patient. It is desirable for such systems to operate in a multiplicity of modes, whereby the mode switching is performed with a high degree of automation. While it is desirable for all the adjustments to be made within the instrument, the use of add-on lenses to expand an OCT instrument's imaging capability, can require the operator to intervene. Switching from one OCT system imaging modality to another, with the concomitant change of optics, can introduce the chance for failure which could yield erroneous results (incorrect measurement or compromised signal strength). Thus there is a need for verification of the optical train prior to any use with a patient to insure that the correct optics were attached by the user and that the system makes any additional configuration adjustments necessitated by the addition of the add-on lens. Moreover, this verification needs also to be robust, meaning little or no chance for it to fail itself.

There have been several approaches to introducing such verification procedures into commercially available clinical products. In one approach, described in U.S. patent application Ser. No. 13/803,522, a diffused feature can be created by painting a small part or area of the lens white or gray. Alternatively, a small area of the housing where the lens is or lenses are held in place can be painted. A light from light source in the ocular lens housing illuminates the diffused feature from behind the lens and is imaged through a light mask onto the instrument's viewing camera. These approaches may have deficiencies in the adequacy and complexity of detection of lenses and their alignments.

SUMMARY

The overall aim of the embodiments presented within the present application is to use OCT measurement data from an OCT system to analyze the optical configuration of the OCT system (e.g. detect the presence, the location, or the alignment of one or more optical components that is part of the optical train). This property, for example, can be automated to facilitate quick conversion from anterior to posterior imaging with appropriate feedback that the changeover has been successfully and correctly accomplished. No additional hardware is required nor any complicated image processing algorithm.

BRIEF DESCRIPTION OF THE DRAWINGS

FIG. 2A represents the situation when there is no add-on or additional lens installed into the beam or optical train. FIG. 2B depicts the situation when an add-on lens has been inserted into the optical train. FIG. 2C shows the situation when two additional lenses are added to the optical train. In these three cases, only alignment along the optical axis is considered. The relative positions of OCT signals presented are representative only and are not absolute in any sense. They demonstrate the relative behavior of signals vs optical configuration as diagrammed.

FIG. 3A and FIG. 3C represents signal sequences that would appear when OCT marginal rays are sent through two lenses, one of which 302 is misaligned. FIG. 3B shows an OCT beam on-axis and the two signals that it would be produced from that particular optical depiction.

DETAILED DESCRIPTION

Figure 1:
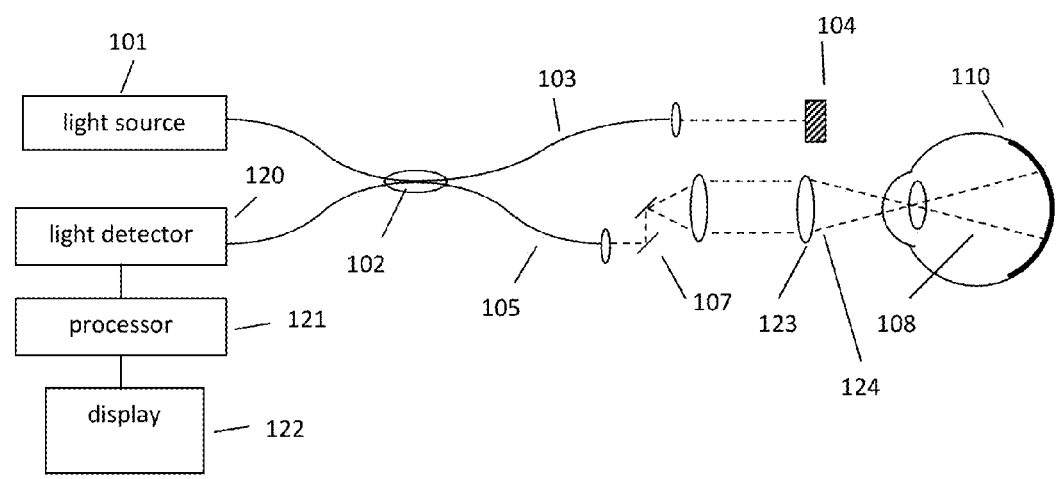
FIG. 1 is a schematic of an optical coherence tomographic instrument based on frequency-domain technology.

A generalized Fourier or Frequency Domain optical coherence tomography (FD-OCT) system used to collect an OCT dataset suitable for use with the present set of embodiments, disclosed herein, is illustrated in FIG. 1. A FD-OCT system includes a light source (101), typical sources including but not limited to broadband light sources with short temporal coherence lengths or swept laser sources.

Light from source (101) is routed, typically by optical fiber (105), to illuminate the sample (110), a typical sample being tissues at the back of the human eye. The light is scanned, traditionally with a scanner (107) between the output of the fiber and the sample, so that the beam of light (dashed line 108) is directed to locations in the sample to be imaged. The optics could deliver a light beam in a one dimensional or two dimensional pattern. Light scattered from the sample is collected, typically into the same fiber (105) used to route the light for illumination. Reference light derived from the same source (101) travels a separate path, in this case involving fiber (103) and retro-reflector (104). Those skilled in the art recognize that a transmissive reference path can also be used. Collected sample light is combined with reference light, typically in a fiber coupler (102), to form light interference in a detector (120). The output signals generated from the detector are supplied to a processor (121). The results can be stored in the processor or displayed on display (122). The processing and storing functions may be localized within the OCT instrument or functions may be performed on an external processing unit to which the collected data is transferred. This unit could be dedicated to data processing or perform other tasks which are quite general and not dedicated to the OCT device. The display (122) can also provide a user interface for the instrument operator to control the collection and analysis of the data.

The interference between the light returning from the sample and reference arms causes the intensity of the interfered light to vary across the spectrum. The Fourier transform of the interference light reveals the profile of scattering intensities at different path lengths, and therefore scattering as a function of depth (z-direction) in the sample.

The profile of scattering as a function of depth along a particular optical ray is called an axial scan (A-scan). A dataset of A-scans measured at neighboring locations in the sample produces a cross-sectional image (slice, tomogram, or B-scan) of the sample. A collection of B-scans collected at different transverse locations on the sample comprises a 3D volumetric dataset. Typically a B-scan is collected along a straight line but B-scans generated from scans of other geometries including circular and spiral patterns are also possible.

The sample and reference arms in the interferometer could consist of bulk-optics, fiber-optics or hybrid bulk-optic systems and could have different architectures such as Michelson, Mach-Zehnder, or common-path based designs as would be known by those skilled in the art. Light beam as used herein should be interpreted as any carefully directed light path. In TD-OCT, the reference arm needs to have a tunable optical delay to generate interference. Balanced detection systems are typically used in TD-OCT and SS-OCT systems, while spectrometers are typically used at the detection port for SD-OCT systems. Embodiments of the present application could apply to any type of optical coherence tomography imaging system.

In FIG. 1, lens (123) is normally called the objective or ocular lens. It is present to produce a focused beam onto a desired part of the eye. In order to accommodate anterior segment (cornea, aqueous humor, and crystalline lens) and posterior segment (vitreous humor and the various retinal tissues down to the sclera), the lens (123) needs to have its focal length adjusted. There are a variety of ways to achieve this, but often a method is to insert or add a negative lens at a position just downstream of its rear vertex (124). Such a lens could be added manually by the user and attached to the system via magnets or any other attachment mechanism known to one skilled in the art. Thus, in this particular approach, addition of this lens to the optical configuration of the system permits the instrument to switch between anterior and posterior imaging. In addition, an add-on lens could be used for pachymetry measurements and which narrows the field-of-view. Alternatively, a field of view wider than is available with the primary lens is desired and a different add-on lens can expand that field-of-view.

The particular depth location being sampled at any one time is selected by setting the path length difference between the reference and sample arms to a particular value. This can be accomplished by adjusting a delay line in the reference arm, the sample arm, or both arms (known herein as an adjustable imaging depth). Typical SD-OCT instruments can image a depth of three to four millimeters at a time. While a frequent adjustment in the reference arm position may be required in SD-OCT to detect and/or characterize the different components in the optical train due to its limited imaging depth, in SS-OCT the additional imaging depth range allowed by a swept-source laser will permit fewer reference arm adjustments. The axial range over which an OCT image is taken (imaging depth, scan depth or imaging range) is determined by the sampling interval or resolution of the optical frequencies recorded by the OCT system. In SS-OCT, it is possible to change the SS-OCT depth range by changing the sweep rate of the source and/or the sampling speed or data acquisition rate of the detector.

It is the aim of the present application to introduce a technique that requires no new instrumentation or equipment and very little additional software to identify the presence, type, and alignment of one or more optical components added to, or within, the optical train of an OCT instrument or system. The basic idea of all embodiments derived therefrom is that the presence or absence of a one or more optical components and their positions and alignments can all be derived from the OCT signal itself. Positions or locations can be any point on any surface associated with a single optical component. The profile of a surface can be approximated with at least two points, though a preferable minimum number should be three.

In canonical optical terminology, and used in the Figures presented in this application, a beam or ray of light appears from the left and proceeds rightward. If this beam of light is collinear with the optical axis of a lens, then the first vertex of a lens that this light strikes will be the front vertex. The next vertex that the light will strike in a lens will be the rear vertex. Thus the beam of light, or the optical ray, encounters one or more surfaces of each detected optical component.

A single A-scan along a single optical ray could suffice to detect a single lens vertex, if the reference arm-sample arm optical path length difference is known in advance for that depth range or longitudinal position. To detect both vertices of a given lens, then an adjustment of the imaging depth may be necessary depending upon the design of the OCT system and/or whether the OCT system is swept-source (SS-OCT) or spectral domain (SD-OCT).

If the position of a lens, for example, is not known in advance then a search pattern has to be conducted to locate it and/or other optical components. To determine the locations of more than one optical component along a given axis, for example the OCT system optical axis, a series of A-scans are required, in which each A-scan is obtained at a certain imaging depth range, and the reference arm-sample arm optical path length difference adjusted for a different, but not necessarily overlapping or consecutive, depth range. These can be assembled (stitched) into one composite A-scan to be analyzed for signal peaks, peak locations, and associating said locations with known optical components. Alternatively, reporting to an operator, such as via a graphical display of the locations, will suffice for a trained operator to recognize problems. One of the preferred embodiments of the present application is to detect, analyze, report, and even align the optical components automatically, so as to remove the potential for operator error.

In another embodiment, a series of composite A-scans can be obtained along several optical rays (e.g., such as marginal, axial, or paraxial) or several pencils of optical rays. These data are then processed to derive positional/location information for a plurality of points on each of the detected optical components. The processed data are then further analyzed to determine optical surface profiles. From the profile information, a lens or optical component can be identified. The totality of information thus derivable becomes: locations/positions of optical components, their identifications, their profiles, and with further processing, their misalignments.

Figure 2:
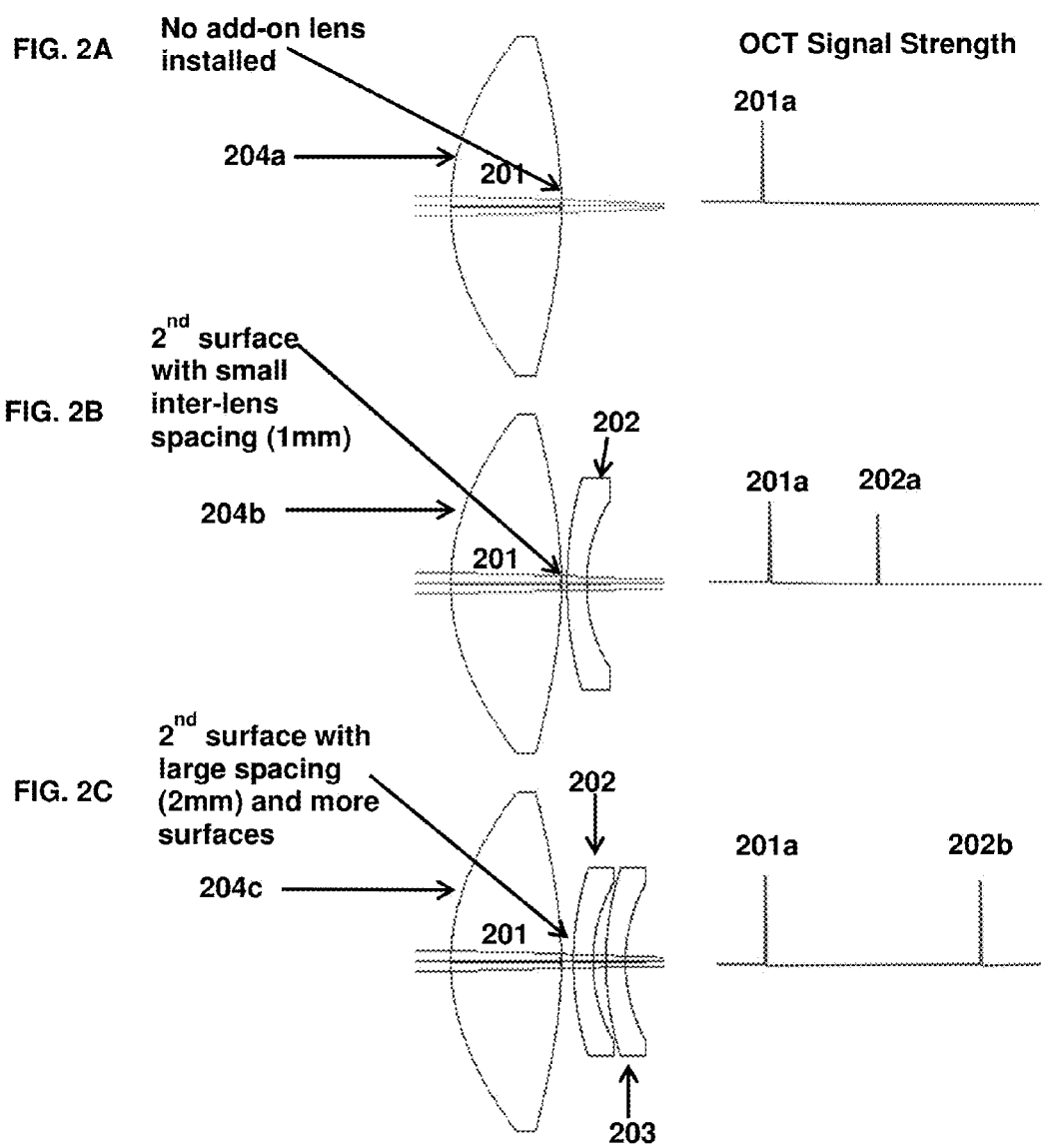
FIG. 2 represents several possibilities for associating positions of optical components with OCT signals.

In FIG. 2, three examples are given of how the OCT signal from an A-scan can be used to detect the presence and position of lenses in the OCT optical train. Optical components could be added to the optical train manually by the instrument operator or automatically by the system based on the imaging mode desired. In one embodiment, the instrument user could be prompted via a message on the system's user interface to add a particular optical component when an imaging mode is selected.

It can be envisioned that a factory calibration procedure would calibrate the presence and identity of optical components, for all imaging modalities (which could include a zoom mode), and produce a stored look-up table for future reference during clinical usage. The arrangement of optical components can be determined in advance and the associated information, such as locations or positions, identifications, optical properties, etc., can be stored in a table known as the pre-determined optical configuration table. This can be done for a variety of optical rays or beams produced by the OCT system. A 'ray' or an 'optical ray,' in the sense used in this application, is one that would be called marginal, axial, or paraxial. It can also refer to a pencil of rays along a marginal or axial direction.

In the case of a single lens (201) (FIG. 2A), e.g., the objective/ocular lens, when an axial beam of light (204a) is sent downstream, there will be a single peak (201a) in the OCT signal along the depth (axial or longitudinal) direction due to the reflection from the rear vertex of the lens. The front vertex will also have an OCT signal peak associated with it, but it will be outside the window set by the current position of the delay line. Changing the delay line position can then allow the detection of the OCT signal peak from the front vertex of the ocular lens should that be desired.

When an additional lens (202) is inserted into the beam (FIG. 2B), close to the rear vertex of the ocular lens (201), upon sending a beam of light downstream (204b), an additional OCT signal peak (202a) will appear in the current OCT signal window allowed by the setting of the delay line position. This second signal (202a) is due to the reflection from the front vertex of the additional lens (202). There will also be an OCT signal from the rear vertex of this lens (202); however, in certain circumstances it will be outside the window allowed by the current setting of the delay line position. The extent of the imaging depth will depend upon the specifics of the design of the optical coherence tomographic system and was discussed above concerning SS-OCT.

In a third example, illustrated in FIG. 2C, again upon sending a downstream beam of light (204c), the second lens (202) is moved axially twice the distance from the ocular lens (201) and a third lens (203) is inserted downstream from that of the second lens (202). In the OCT signal window, the original peak (201a) is still present, but with the increase in separation between lens (201) and (202), the position of the peak due to the front surface of (202) has shifted from (202a) in FIG. 2B to (202b) in FIG. 2C. Thus the OCT signal from an A-scan can be used not only to detect if an additional lens has been inserted, but if it is located at the proper distance from a reference point.

Establishing the proper distance between the ocular lens (or the last lens of the OCT prior to the eye) and the apex of the corneal surface of a patient is important prior to any clinical application, such as pachymetry, corneal power measurements, or retinal scanning.

Figure 3:
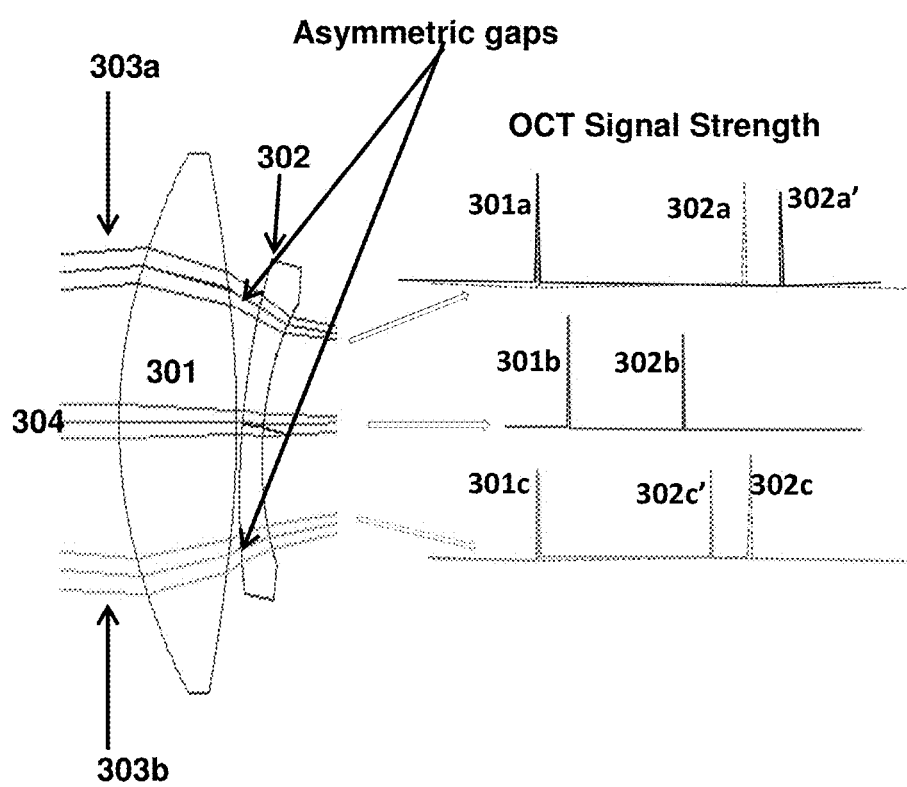
FIG. 3 demonstrates that misalignment of optical components can be detected with OCT signals. The relative positions of OCT signals presented are representative only and are not absolute in any sense. They demonstrate the relative behavior of signals vs optical configuration as diagrammed.

Angular misalignment of a lens in an OCT beam can also be checked by the use of the OCT beam. In FIG. 3, two lenses (301) and (302) are present in the optical train of the system, and are illuminated with three beams of OCT light: two marginal OCT beams (303a) and (303b), and an axial OCT beam (304). While FIG. 2 or 3 are two-dimensional schematics of three-dimensional objects, it should be clear that these 2D cases are entirely applicable to the three-dimensional situation. Angular misalignments in any plane containing the lens or optical element relative to the optical axis can be derived using the embodiments described herein.

FIG. 3 demonstrates how misalignment (e.g., tilt or tip relative to the optical axis, or positional offset along that optical axis) of a lens can be detected based upon at least two OCT measurements. An on-axis (304) exemplar (FIG. 3B) is given as a reference. Two additional cases are illustrated and are generated by selectively sending a marginal OCT pencil beam above (303a) (FIG. 3A) and below (303b) (FIG. 3C) the optical axis, and preferably equidistant about the optical axis. (Again, this is just a 2D explanation of a 3D approach.)

In FIG. 3, the first lens (301) is assumed, in this exemplar, to be aligned, and the second lens (302) is assumed to be tilted, with the upper edge of the second lens (302) further away from the first lens than nominal, while simultaneously, the lower edge of the second lens (302) is closer to the lower edge of the first lens (301) than nominal. Thus the upper and lower gaps between the two lenses are not the same. The existence of asymmetric gaps can then be sensed by sending an OCT beams (303a) and (303b) at positions equidistant from the optical axis and measuring the resultant signals as will be explained in detail below.

FIG. 3A illustrates the use of the OCT signal when the upper portions of the two lenses (301) and (302) are further away that ideal. Based on the delay line location, the first peak (301a) detected will be from that of the rear surface of (301) at that meridian, which is detected earlier than the signal (301b) from the rear vertex of lens (301) (the on-axis signal). The second peak (302a') detected will be from that of lens (302), but delayed from that of its nominal or aligned position (302a), as the (302) lens at that point is displaced further than nominal.

Using a variety of marginal pencils of rays, e.g., (303a) and (303b), can one determine misalignment of the lenses. In case (B), there is no identification of misalignment, as both detected signals, the first (301b) from the rear vertex of lens (301) and the second (302b) from the front surface of the second lens (302), are on axis.

In the case depicted in FIG. 3C, with a lower marginal beam of light (303b), the first signal detected (301c) should be at the same location as that of (301a), assuming that lens (301) has a symmetric profile about the rear vertex and has been properly aligned with respect to the optical axis of the OCT optical train. The second peak detected (302c') will be that of the misaligned lens (302), which at this point is closer to lens 301 than the location where it should ideally be indicated by peak (302c). If lens (302) is properly aligned, then (302) and (302c) would be located at the same point in the OCT signals.

Another embodiment of the present application uses a plurality of pencil beams at differing marginal positions, to detect misalignment of optical components. Moreover, the front or rear surface profiles of a lens can be mapped out and compared with design or manufactured values found in the pre-determined optical configuration table. With this comparison, it can be determined if the optical axis of a lens, for example, is acollinear or oblique with respect to the optical axis of the OCT optical train, and/or whether the lens is the correct one.

Thus, by the use of a multitude of marginal ray OCT beams, the alignment of the detected lenses relative to the optical axis can be derived. Axial and/or paraxial rays or pencils of ray can also contribute to the determination of the observed optical configuration. This information, such as locations or positions, properties such as optical profiles and identifications can be stored in an observed optical configuration table, Once this table has been determined, it can be compared with what is expected by a comparison with the pre-determined optical configuration table.

A preferred embodiment is obtaining OCT A-scan data at a pair of marginal rays approximately equidistant and diagonally opposite from the optical axis. This would yield the level of tilt of that lens relative to a first plane containing the optical axis and a line between the two marginal rays. This process can be repeated using other pairs of diagonally opposite marginal rays to derive tilts or tips in planes perpendicular to the first plane. Thus the overall misalignment of a particular element can be derived. Moreover, in another embodiment, processing several marginal ray A-scans would yield the approximate profiles of the lenses, thus permitting identification of the various lenses and their positions within the optical configuration. The rays do not necessarily have to be either diagonally opposite or equidistant from the OCT optical axis to determine a tip/tilt.

Figure 4:
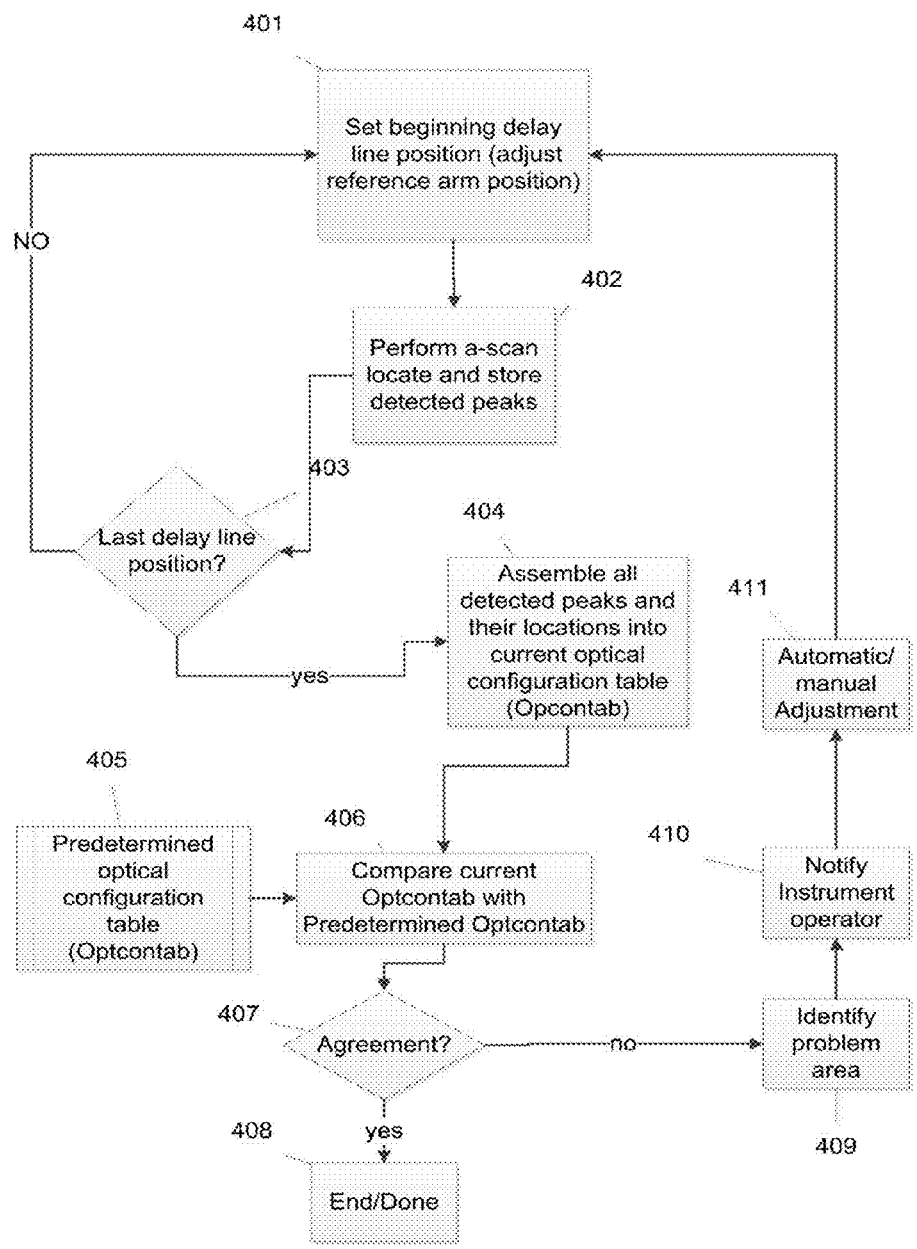
FIG. 4 is a flow chart of a procedure to carry-out an overall configuration check of the optical components of the instrument according to one embodiment of the present application.

An algorithmic approach of the present application can be summarized in the flow chart of FIG. 4. At the beginning of what might be called an optical configuration check, the reference arm is set to a certain position (401), then a set of axial scans are produced where the delay line position is changed between scans as needed to image the optical train or portions thereof, with subsequent signal peaks located and recorded (402). If this is the last reference arm position (or delay line position) (403), then all of the detected peaks and their locations are stored into a table (404) or database called the pre-determined optical configuration table (opcontab). This just-determined or current opcontab (404) is then compared (406) with a factory determined one (405) and if there is agreement (407), then the sanity check phase is completed (408) and the instrument is ready for clinical applications. If the two tables are not in agreement (407), then the processor identifies the area of difficulty (409), notifies the operator of the discrepancy (410) and perhaps offers either a manual fix to be enacted or allows the processor to attempt a correction (411). If the problem has been allegedly fixed, then the entire configuration check is performed again until agreement has been reached between the factory pre-determined opcontab (405) and the current or observed opcontab (404). Different optical configuration tables could exist for different lens configurations. If a particular imaging mode is selected and the processor determines that the correct lens for that imaging mode has been attached via comparison to the system's look-up table, the system could make additional changes like delay line adjustments or shifting of lenses that might be required to collect images in that particular modality.

In the case of SS-OCT, which can possess an extended imaging depth, readjustment of the reference arm relative to the sample arm will be needed less often as with SD-OCT. As described above, such an extended depth can be implemented, in which case the reference arm may not need be readjusted for the detection of those optical components of the OCT optical train that are in close proximity—within the extended imaging depth of SS-OCT.

In the situation as depicted in FIG. 2C, where lenses (201), (202), and (203) are in close proximity, the rear vertex, and the vertices of (202) and (203) could be detectable in a single SS-OCT A-scan, depending upon their physical separation.

In an alternative embodiment, a plurality or multiplicity of A-scans taken along a given optical ray direction but at different longitudinal (or z-axis or depth) positions, achieved by manipulation of the reference arm-sample arm relative optical path length, can be stitched together to form a composite A-scan. Such a composite A-scan can then be processed like the individual A-scans mentioned hereinabove, to discover the signal peaks and their locations associated with one or more optical components. If this composite A-scan has been derived from scans taken along the optical axis of the OCT system, then the signal peaks would be approximately correlated to the various vertices of the lenses.

Use of the Cornea in Optical Configuration Detection

Another embodiment of the present application is to use the OCT instrument to observe one or more corneal surfaces of a real or of a model eye, and determine if the derived curvatures are within an normative range of such measures. Unlike the previously discussed procedure, wherein individual lenses are detected and their locations and alignments are characterized, in this particular embodiment, images in the form of one or more B-scans are analyzed to distinguish whether the optical configuration is the correct one. This could be particularly useful when a single optical component (e.g. a single lens or lens group) is added to the optical train to change the imaging mode of the system. For this embodiment, a single B-scan would suffice for the determination.

The detected surfaces could also be those of the crystalline lens. The corneal surface curvature derived from at least a single B-scan could be that of any detected part of the either corneal surface (anterior or posterior). If one or more B-scans are tilted such that the vertex of the cornea is not at the center of the image, then a rotation can be performed using standard transformation equations.

In either ocular optic, cornea or crystalline lens, the range of curvatures (or equivalently, radii of curvatures) are well-known and would be included in a normative database to which the observation or observations are compared. The observations can be raw, and thus the entries in the normative database also have to represent raw images of surfaces in the anterior segment. Alternatively, the images can be processed to remove various artifacts, and thus the normative database could also possess such processed information.

Figure 5:
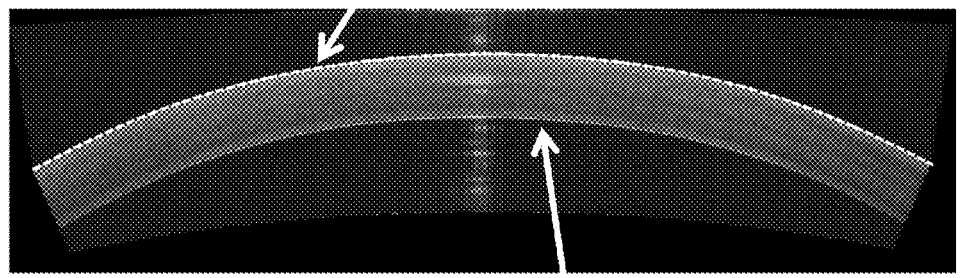
FIG. 5 is a B-scan of a model cornea with the correct lens inserted. The anterior corneal surface (501) is easily detected as is the posterior corneal surface (502). The dashed curve is the segmentation. The anterior surface has been dewarped. (See US2013208240 for an explanation of dewarping and segmentation.)
Figure 6:
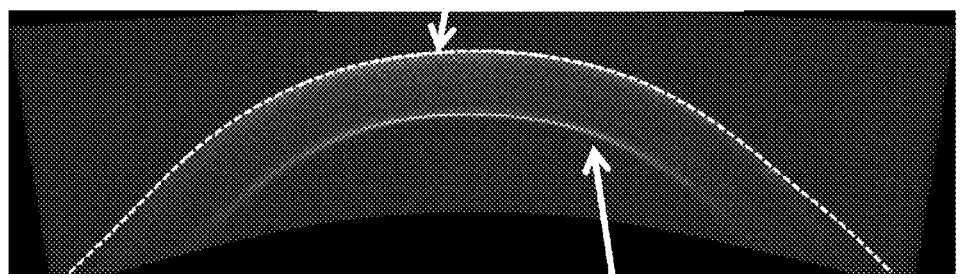
FIG. 6 is a B-scan of a cornea with the incorrect lens inserted. The anterior corneal surface (601) is easily detected as is the posterior corneal surface (602). The dashed curve is the segmentation. The anterior surface has been dewarped.

To demonstrate the applicability of this technique, reference is made to FIG. 5, which shows a B-scan of the cornea in which the OCT instrument has the correct optical configuration for observing the anterior segment of the eye. The corneal surfaces 501 (anterior) and 502 (posterior) are detected with good signal-to-noise and display an expected curvature. In FIGS. 5 and 6, the corneal anterior surfaces have been dewarped and the segmentation displayed as dashed curves. (An explanation of segmentation and dewarping may be found in US2013208240.)

FIG. 6 depicts a B-scan of the cornea for the case when an OCT instrument possesses an incorrect optical configuration, leading to substantially altered appearance of the cornea. The detected corneal surfaces 601 (anterior) and 602 (posterior). Comparing the curvatures of the anterior surfaces between these two FIG. 501 vs 601, or 502 vs 602) reveals a significant difference and could therefore be used to alert the operator to the incorrect configuration or even initiate an automated configuration check within the system.

The anterior surfaces in both FIGS. 5 and 6 were analyzed for corneal curvatures. Using the correct lens (add-on), the radius of curvature is 8.03 mm. In the case of the wrong lens, the radius of curvature is 3.23 mm. There is no known adult population that possesses a corneal radius of curvature as low as 3.2 or even as low as 6.4 mm. The average for an adult population is about 8 mm.

Shape Metrics

A shape metric is a metric that is correlated to some geometric profile of a 2D or 3D surface. Discussed below are several possible definitions of shape metrics that can be used to separate corneal scans taken with a correct optical configuration from ones that have been obtained with a wrong configuration. Precise shape metrics are defined, such that a method of optical configuration identification can be performed automatically, and thus have the ability to notify an operator that the instrument possesses the wrong optical configuration.

In one embodiment comprising the use of shape metrics, the anterior surface data derived from a plurality of OCT B-scans are used to reconstruct the corneal surface model. A map of the axial curvature of the corneal surface can then be created by computing the axial curvatures at all surface points. These calculations are based on sampling the axial curvature map with the x, y coordinates of corneal surface at a given zone diameter with the same elevation (i.e., radius about the apical axis).

The method for determining curvatures can be summarized as follows: one or more B-scans of the cornea (or anterior segment) are obtained. Canny edge detection is performed (Canny 1986), resulting in a binary image where a pixel having a "1" value represents an edge. Canny edge detection produces an edge image that most likely contains all the surface edges of interest. The problem is that these edges are not labeled and cannot be used without further processing. The edge information can be used to estimate the initial positions of the anterior surface. Connected edges with a length smaller than a threshold are removed to reduce the execution time in the next step. The anterior surface has been selected only as a representative surface found in the anterior segment. Other surfaces may be of similar use in this embodiment.

In the case of a single B-scan (2D), quadratic functions (parabolic forms) are then robustly fitted to identify connected edges. The number of quadratic functions that are fitted depends on the number of connected edges found in the selected region of interest (ROI). This number may be significantly more than the anatomical edges found in the sample because many of the "edges" identified by Canny edge detection may be due to noise, and others may be due to the mirror or complex conjugate image of the iris.

In the case of multiple B-scans (i.e., 3D), quadric functions are then robustly fitted to identify connected edges. The number of quadric functions that are fitted depends on the number of connected edges found in the ROI. A similar as outlined in the previous paragraph regarding noise detections also will exist in the processing of 3D data.

The quadric surface $z=f(x,y)$ models the corneal data in a general form and includes the different shapes such as ellipsoid, paraboloid, and hyperboloid. The quadric surface given by the general equation:

$$a_{11}x^2+a_{22}y^2+a_{33}z^2+a_{12}xy+a_{13}xz+a_{23}yz+a_1x+a_2y+a_3z=0 \quad (1).$$

The coefficients ($a_{11}$, $a_{22}$, $a_{33}$, $a_{12}$, $a_{13}$, $a_{23}$, $a_1$, $a_2$, $a_3$) are found by fitting the corneal data using RANSAC robust fit. (For RANSAC fitting, see M. A. Fischler and R. C. Bolles 1981.) Setting one or more of these coefficients to zero a priori results in a more specific form for the fit.

The quadric fitting may fail to produce a good fit for a difficult data set. It may be necessary to center the data prior to an attempted fit. Centering the data (subtracting the mean $<z>$ from each value) reduces the degree of multi-collinearity. (This term refers to a situation in which two or more independent variables in a regression model have a correlation near one.)

From the functional form fitted to the connected edges, one fit is identified as corresponding to the anterior surface and is used for the determination of curvatures. Alternatively, other identified surfaces can also be used. In the case of the two functional forms mentioned hereinabove, both are assumed to have a concave profile, and to have a vertex that is located approximately in the central portion of the image or images.

The fitting parameters (also shape metrics) extracted from either a quadratic or a quadric fit can then be used to discern if the optical configuration of the OCT system is the correct one. The computed parameters in a particular case would then be compared with equivalent parameters derived from data taken with a correct optical configuration, to segregate false optical configuration from the desired optical configuration.

An alternative approach would be to determine the axial curvatures of the data from the B-scans. (See, e.g., Klein et al. 1997 for a discussion of axial curvature and its possible definitions: normal curvature, marginal curvature, mean curvature, or Gaussian curvature.) This would be performed subsequent to the fitting procedures outlined above. Axial curvature should not be confused with axial power, as the former concerns corneal shape or geometry, whereas the latter is more related to refractive properties of the cornea.

The axial curvature at a given point (x, y, z) on the corneal surface is defined as the distance along the surface normal ($n_x$, $n_y$, $n_z$) from the point of interest to the optical axis, e.g., one of the corneal vertices. The axial curvature map of the cornea can be determined by computing the axial curvatures at all surface points.

Figure 7:
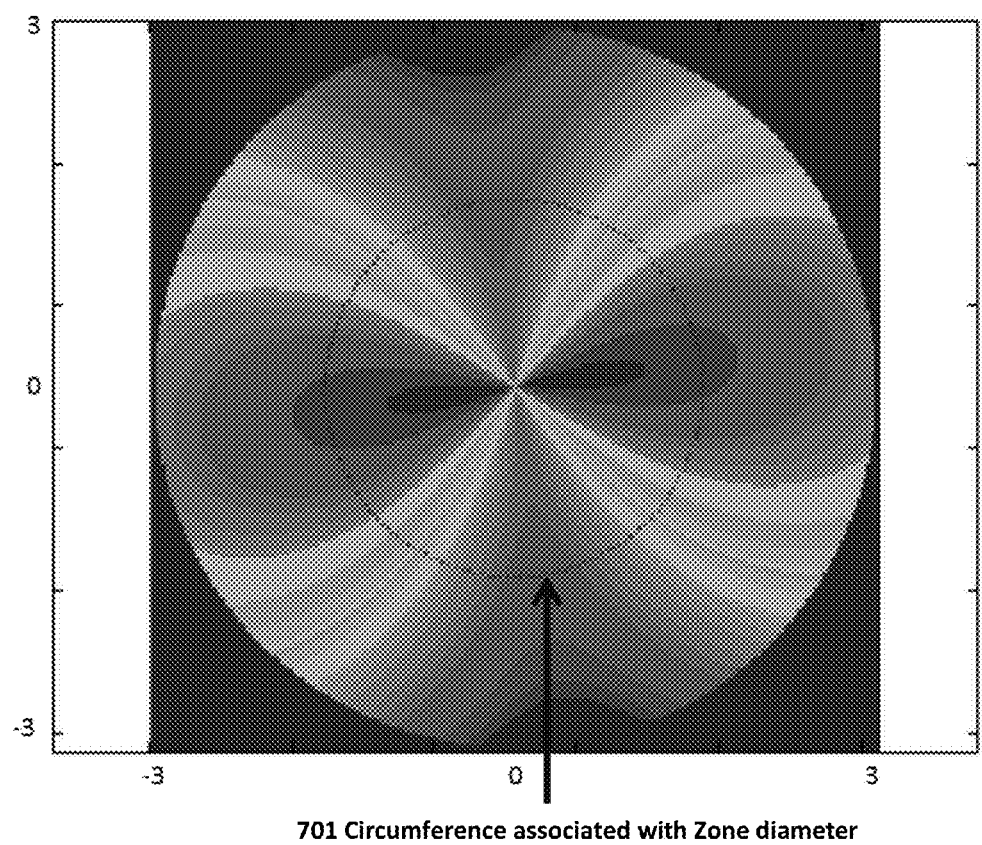
FIG. 7 is the axial curvature map and sample axial curvature data. The ordinate and abscissa are the lateral coordinates of the OCT scans. Each pixel in this map represents the value of the axial curvature projected onto a plane that is perpendicular to the apical radius and is located at a certain elevation below the apex or, equivalently, perpendicular to a specific point along the apical radius. An alternative but equivalent viewpoint would be at a specific radius or diameter perpendicular to the apical radius. The latter being referred to as the zone diameter (701) or the circumference equivalent to that diameter.

If 3D or multiple B-scans have been obtained, then a map of the axial curvature can be obtained. An example of a map is depicted in FIG. 7, with the x, y coordinates (given in mm) of corneal surface at a given zone diameter FIGS. 7-9, (701) (depending on the eye shape and curvature) with the same elevation, which, in this case, is at a radius of 1.5 mm. Note that the zone diameter (701) can be determined for each eye based on the corneal radius/power at the vertex using the formula:

$$D = \frac{d}{(2.4)(2)(0.1527)R} \quad (2)$$

where d=a fixed given ring measurement zone diameter (e.g. 2.4 mm or 3.2 mm) and R=corneal radius of curvature at the vertex for the nominal zone of 2.4 mm. The value of each pixel in FIG. 7 is of an axial curvature as derived from fitting the ensemble of OCT B-scans.

An example illustrates the utility of this approach. OCT data are obtained of a real cornea. From a point 1.5 mm away from the corneal apex, the radius of curvature using the correct lens is 8.452 mm. In the case of imaging same with the wrong lens, the radius of curvature is 4.331 mm. In both of these cases the values were determined at a zone diameter of 3 mm. (This diameter is the traditional value used to determine corneal power.) There is no known adult population which possesses a radius of curvature as low as 4.3 mm.

Figure 8:
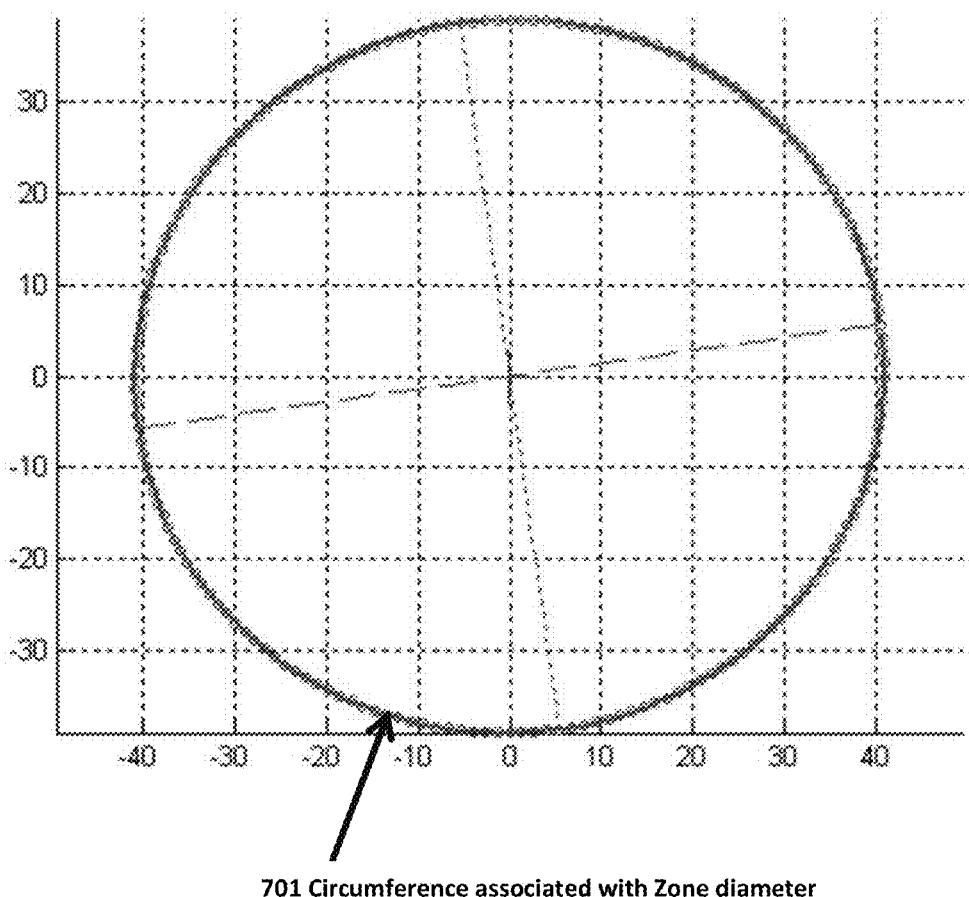
FIG. 8 represents the axial curvature data and the best fit ellipse with the major and minor axes indicated. It is derived from the information conveyed in FIG. 7. The ordinate and abscissa are the same as in FIG. 7. The zone diameter (701) is identified.

FIG. 8 depicts the axial curvature, given in Diopters, for the lateral x and y coordinates, and was taken at the radius of 1.5 mm from the center of the ellipse from the data shown in FIG. 7. The two orthogonal lines depicted in this FIG. 8, are the major and minor axes of the ellipse obtained at a the desired elevation (radius=1.5 mm).

In another embodiment, an alternative to the axial curvature or axial curvature map, two parameters or dual shape metrics can be used to define essentially the shape of the cornea: asphericity and apical radius of curvature.

The equation that models a corneal surface is one based on a revolution of a conic surface about an apical axis:

$$C(r, Q) = \frac{r - \sqrt{r^2 - (Q+1)\rho^2}}{Q+|1} \quad (3)$$

where r and Q are the apical radius and asphericity (i.e., conic constant), respectively. The apex of the profile is at the origin of a polar coordinate system. The raw OCT image may be used to fit Eq. (3) or one that has been transformed by dewarping, as has been discussed hereinabove. While these parameters are commonplace in corneal topographic evaluations, they might be subjected to unwanted variations due to problems such as keratoconus. The average Q values ranges from −0.42 to −0.26 (Benes et al. 2013), and is a fairly tight distribution as exemplified by FIG. 2 of Benes et al. (2013).

Figure 9:
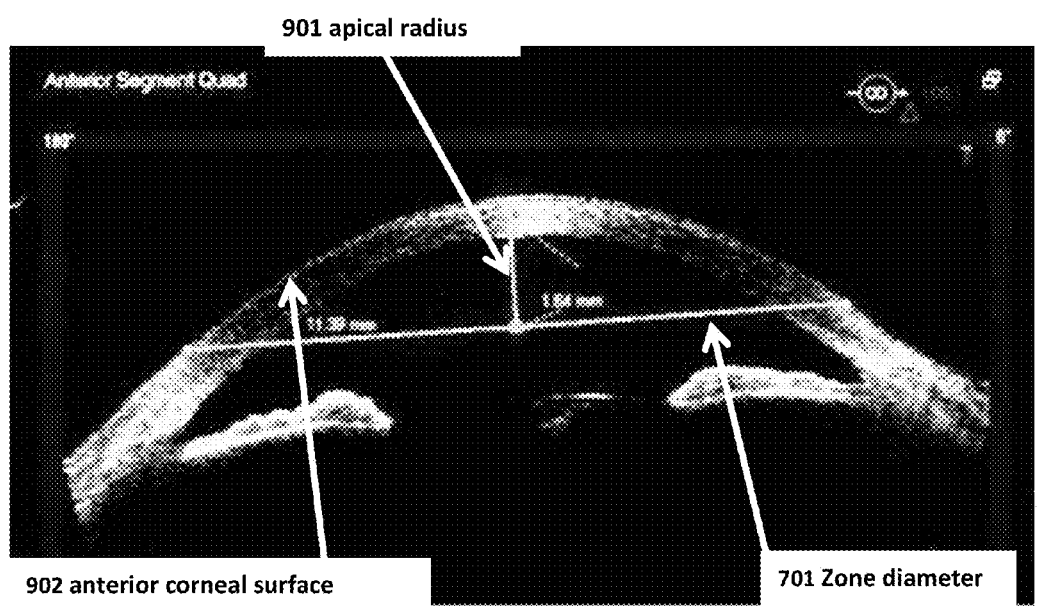
FIG. 9 depicts an image of a cornea, with the anterior surface (902) located. The chosen apical radius is indicated (901), as is the (701) zone diameter. The chosen distance along this apical radius is 1.64 mm which will then correspond to the zone diameter of 11.39 mm.

An alternative approach is to separate the two modes (right lens/wrong lens) by defining a chord such as the one depicted in FIG. 9. In this case, the chord (zone diameter from a single scan, for example, 701) is the one that perpendicularly intersects a given point on the apical radium (901). In the case of FIG. 9, this point is 1.64 mm below the anterior surface (902) apex. Based on this approach, other such shape metrics can be readily devised by the person of ordinary skill in the art.

While the above discusses the analyses of B-scans, A-scans can also be used in the fitting process, albeit with substantial greater error due to the paucity of data. A-scans can be obtained of the corneal surfaces at least with a sufficient density that a surface fit can be reliably performed. With this information, a derivation of corneal surface curvature (or other metrics) can be derived and compared with a normative database.

In any of the aforementioned embodiments, shape metrics can be used either with raw OCT images or processed ones, as discussed above. In either case, the normative ranges of any shape metric or metrics used will need to be established so as to be able to discern the differences between correct and incorrect optical configurations. The derived metrics would then be compared with a range of expected values obtained from normative databases.

Although various applications and embodiments that incorporate the teachings of the present invention have been shown and described in detail herein, those skilled in the art can readily devise other varied embodiments that still incorporate these teachings. Although the description of the present invention is discussed herein with respect to the sample being a human eye, the applications of this invention are not limited to eye and can be applied to any application using OCT.

The following references are hereby incorporated by reference:

Patent Documents

US20070291277
U.S. Pat. No. 7,830,525

U.S. Pat. No. 6,095,648
US20110102802
US20080106696
US20110176111
US20120262720
US2013208240
U.S. patent application Ser. No. 13/803,522

Non-Patent Literature

Leitgeb et al. 2004, Ultrahigh resolution Fourier domain optical coherence tomography, Opt Exp 12, 2156-2165.
Hee et al. 1995, "Optical Coherence Tomography for Ophthalmic Imaging," *IEEE Engineering in Medicine and Biology* 14, 67-75.
Canny 1986, IEEE Transactions on Pattern Analysis and Machine Intelligence PAMI-8(6), 679-98.
M. A. Fischler and R. C. Bolles 1981, Comm. of the ACM 24(6), 381-95.
Klein 1997, Optom Vis Sci 74(11), 931-944.
Gatinel et al. 2011, Cornea 30(5), 508-515.
Gatinel et al. 2002, J. Fr. d'Ophthalmol 25(1), 81-90.
Gonzalez-Meijome et al. 2007, J. Cataract Refract Surg 33, 465-473.
Klein 2000, OSA Tops Vol 35, Vision Science and its Applications, 286-296.
Gatinel et al. 2004, Inves Ophthal Vis Sci 45(5), 1349-1359.
Klein 1997, Optom Vis Sci 74, 931-944.
Benes et al. 2013, Coll Antropol 37, Suppl. 1, 117-120.
Klein & Mandell 1995, Invest Ophth Vis Sci 36(10), 2096-2109.

It is claimed that:

1. A method of operating an optical coherence tomography (OCT) system to identify the presence, location or alignment of one or more lenses of an OCT system, said OCT system including a light source generating a beam of radiation that is divided along a sample path and a reference path, said system having an adjustable imaging window wherein a relative optical path length between the reference arm and the sample arm can be changed to adjust the location of the imaging window, said method comprising:
   setting the imaging window to be aligned with the likely location of the lens to be identified;
   obtaining OCT measurement data from said imaging window;
   evaluating the OCT measurement data to detect the location of signal peaks;
   comparing the location of the signal peaks with data stored in an optical configuration table with expected lens information to identify the presence, the location, or the alignment of the lens; and,
   displaying or storing the results of said.

2. A method as recited in claim 1, wherein the OCT measurement data comprises one or more A-scans taken along an optical ray.

3. A method as recited in claim 1, in which the lens is an add on lens.

4. A method as recited in claim 1, further comprising:
   automatically adjusting the optical configuration of the OCT system based upon the results of the comparison.

5. A method as recited in claim 1, in which the results of the comparison includes determining one or more misalignments of the optical components.

6. A method as recited in claim 1, further comprising;
   obtaining a plurality of collinear A-scans at a plurality of imaging depths along the same optical ray;
   combining said collinear A-scans into a composite A-scan; and,
   processing said composite A-scan to detect signal peaks and locations of said signal peaks.

7. A method as recited in claim 6, further comprising;
   comparing said locations with entries in the optical configuration table; and,
   displaying, or storing, the results of said comparison.

8. A method as recited in claim 1, further comprising:
   obtaining a plurality of collinear sets of A-scans, in which each collinear set of A-scans was taken along a different optical ray by the OCT system;
   combining the collinear set of A-scans into a set of composite A-scans;
   further processing the set of composite A-scans into a collection of locations of signal peaks;
   comparing the collection with entries in the optical configuration table; and,
   displaying, or storing, the results of said comparison.

9. A method to identify the correctness of an optical configuration of an optical coherence tomographic (OCT) system comprising:
   obtaining OCT measurement data of the eye of a patient;
   identifying a corneal surface within the OCT measurement data;
   processing said data to determine a metric that defines the shape of the identified corneal surface;
   comparing the determined shape metric of the identified corneal surface with normative ranges of metrics of corneal surfaces stored in a database to determine whether the determined shape metric of the identified corneal surface falls within the normative ranges and if not, identifying the optical configuration as incorrect; and,
   displaying or storing the results of the comparison.

10. A method as recited in claim 9, wherein the OCT measurement data comprises one or more B-scans.

11. A method as recited in claim 10, in which the determined shape metric is based on the curvature of the corneal surface.

12. An optical coherence tomographic (OCT) system for imaging a sample, comprising:
   a light source for generating a beam of light;
   a divider for splitting the beam along separate sample and reference paths;
   means for adjusting the path length difference between the sample and reference paths to define the location of an imaging window;
   optics for directing the light over one or more locations on the sample;
   a detector for receiving interfered light returned from both the sample and reference paths; and,
   a processor for analyzing signals generated by the detector, in which said processor locates the presence, location, and the alignment of a lens of the OCT system based upon said signals, wherein the path length difference between the sample and reference paths is selected to align an imaging window with the likely location of the lens to be identified allowing OCT measurement data to be collected within the imaging window, said processor for evaluating the OCT measurement data to detect the location of signal peaks and comparing the location of the signal peaks with data stored in an optical configuration table with expected lens information to identify the presence, the location, or the alignment of the lens.

13. A system as recited in claim 12, in which said processor also functions to report to the user, store or further process the results of said comparison.

14. A system as recited in claim 1, in which said processor also functions to adjust the lens based upon the results of the comparison.

15. A system as recited in claim 14, in which the lens is automatically adjusted.

16. A method as recited in claim 9 wherein the corneal surface is the anterior corneal surface.

17. A method as recited in claim 9 wherein the corneal surface is the posterior corneal surface.

\* \* \* \* \*

UNITED STATES PATENT AND TRADEMARK OFFICE
CERTIFICATE OF CORRECTION

PATENT NO. : 9,545,199 B2
APPLICATION NO. : 14/489352
DATED : January 17, 2017
INVENTOR(S) : Yingjian Wang et al.

It is certified that error appears in the above-identified patent and that said Letters Patent is hereby corrected as shown below:

In the Specification

In Column 12, Line 2, after "at" delete "a".

In the Claims

In Column 13, Line 53, in Claim 1, delete "said." and insert -- said comparison. --, therefor.

In Column 15, Line 4, in Claim 14, delete "claim 1," and insert -- claim 13, --, therefor.

Signed and Sealed this
Seventeenth Day of April, 2018

Andrei Iancu
*Director of the United States Patent and Trademark Office*